United States Patent [19]

Bonneau

[11] Patent Number: 4,987,245
[45] Date of Patent: Jan. 22, 1991

[54] ORGANOTIN FLUORIDES HAVING CONTROLLED MORPHOLOGY

[75] Inventor: Lionel Bonneau, Salindres, France

[73] Assignee: Rhone-Poulenc Chimie, Courbevoie, France

[21] Appl. No.: 421,945

[22] Filed: Oct. 16, 1989

[30] Foreign Application Priority Data

Oct. 14, 1988 [FR] France .................................. 88 13529

[51] Int. Cl.$^5$ ................................................. C07F 7/22
[52] U.S. Cl. ...................................... 556/104; 556/103
[58] Field of Search ..................... 556/104, 103, 95, 87

[56] References Cited

U.S. PATENT DOCUMENTS

| | | | |
|---|---|---|---|
| 4,036,866 | 7/1977 | Larkin et al. | 556/103 |
| 4,254,046 | 3/1981 | Franz et al. | 556/104 |
| 4,322,363 | 3/1982 | Wagner | 556/104 |
| 4,510,095 | 4/1985 | Holland et al. | 556/103 X |
| 4,694,091 | 9/1987 | Kerherve et al. | 556/104 |

Primary Examiner—Arthur C. Prescott
Attorney, Agent, or Firm—Burns, Doane, Swecker & Mathis

[57] ABSTRACT

Organotin fluorides, notably dialkyltin difluorides, well adpated for the manufacture of coated insulating glassware and having controlled morphology, are prepared by reacting a stannic compound, e.g., an organotin chloride, with a fluorinating agent, e.g., hydrofluoric acid or an ammonium fluoride, admixing the organotin fluoride thus produced in a solvent that is immiscible with the fluorinating agent but which solubilizes the organotin fluoride therein, subsequently or simutaneously heating the solvent medium to a temperature sufficient to release unreacted fluorinating agent therefrom, and cooling such solvent medium and thereby crystallizing therefrom an organotin fluoride having a controlled morphology, e.g., well defined platelets having a characteristic DTA spectrum.

22 Claims, 1 Drawing Sheet

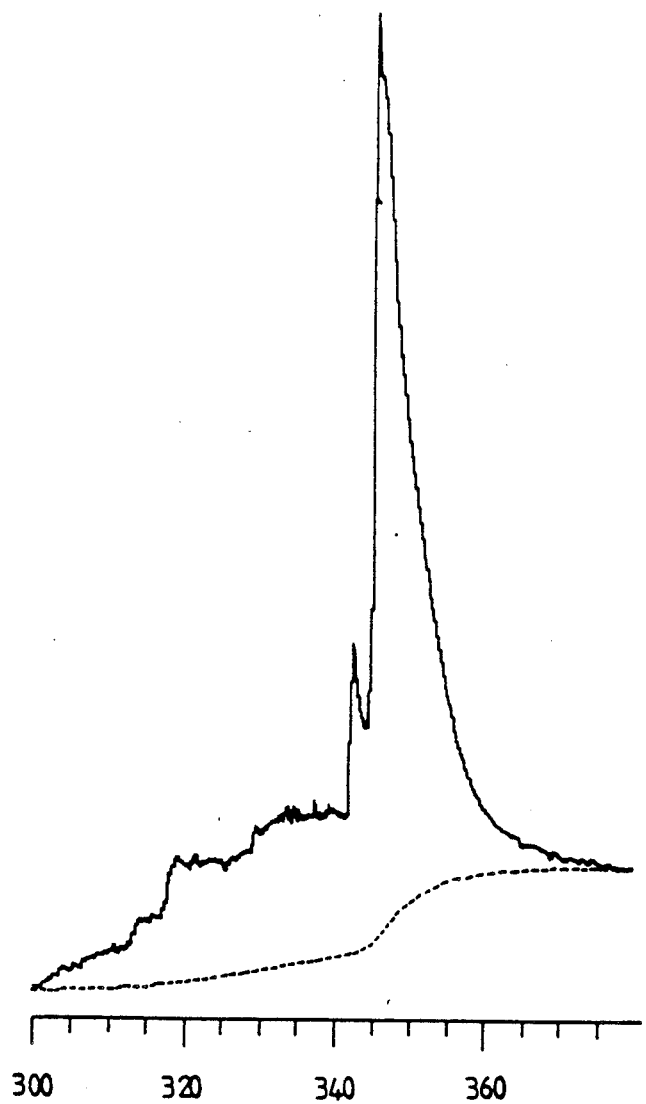

ORGANOTIN FLUORIDES HAVING CONTROLLED MORPHOLOGY

BACKGROUND OF THE INVENTION

1. Field of the Invention:

The present invention relates to novel organotin fluorides, and, more especially, to novel dialkyltin fluorides having controlled morphology and to a process for the preparation thereof.

2. of the Prior Art:

Dibutyltin fluoride (DBTF) is a known compound particularly useful for the manufacture of insulating glasses which reflect infrared radiation.

For this application ("hardcoating"), DBTF is deposited onto the glass in a layer of predetermined thickness. Accordingly, a product is required that is not heterogeneous, i.e., it must have a well defined grain size distribution of about 10 $\mu$m and a highly specific platelet morphology. It should also be available in the form of a powder, which itself should not be adhesive.

Several processes are known to this art for the preparation of organotin fluorides and specifically DBTF. These processes entail reacting a fluorinating agent with a stannic substrate.

Exemplary such fluorinating agents include the alkali metal fluorides such as KF, ammonium fluoride, and aqueous or anhydrous hydrofluoric acid. Exemplary such stannic substrates include dibutyltin oxide, dibutyltin chloride and dibutyltin acetate.

The reaction may be carried out in an aqueous or methanol medium, for example in aqueous HF, or in anhydrous HF alone.

All of the prior art processes, however, in addition to their specific disadvantages, present one major common defect. Indeed, each produces a product having a highly variable morphology.

Accordingly, serious need exists in this art for organotin fluorides having a controlled morphology, in particular organotin fluoride in the form of platelets and having a restricted grain size distribution.

SUMMARY OF THE INVENTION

Thus, a major object of the present invention is the provision of novel organotin fluorides having a controlled morphology and which otherwise avoid those disadvantages and drawbacks to date characterizing the state of this art.

Briefly, the present invention features, in a first embodiment thereof, the preparation of an organotin fluoride by reacting a fluorinating agent with a stannic substrate and which comprises (a) admixing the organotin fluoride thus produced in a solvent that is immiscible with the fluorinating agent but which solubilizes the organotin fluoride, (b) subsequently or simultaneously heating the solvent medium thus formulated to a temperature sufficient to release the fluorinating agent therefrom, and (c) cooling such solvent medium and thereby crystallizing said organotin fluoride.

In a second embodiment of the invention, a stannic substrate, a fluorinating agent and a solvent that is immiscible with the fluorinating agent but which solubilizes the desired organotin fluoride are intimately admixed and, following the reaction of the fluorinating agent with the stannic compound, heating the admixture to a temperature sufficient to release the fluorinating agent, and then cooling the reaction mixture and thereby crystallizing the organotin fluoride.

BRIEF DESCRIPTION OF THE DRAWINGS

The Figure of Drawing is a differential thermal analysis (DTA) spectrum of a dibutyltin difluoride according to the invention.

DETAILED DESCRIPTION OF THE PREFERRED EMBODIMENTS OF THE INVENTION

More particularly according to the present invention, an organotin fluoride is thus produced essentially comprising uniform platelets having a high purity.

Indeed, the dialkyltin fluorides of the invention are characterized in that they are present in the form of platelets having a length of 25 to 100 $\mu$m, a width of 5 to 20 $\mu$m and a thickness of 0.02 to 1 $\mu$m and in that they exhibit a DTA spectrum having an exothermic peak at about 350 C.

This invention also features the organotin fluorides, per se, notably dibutyltin difluoride, having the above morphological characteristics and DTA spectrum.

The invention also features the use of the above novel compounds in the manufacture of insulating glasses.

As indicated above, the process of the invention comprises treating a previously prepared organotin fluoride, or one that is prepared in situ, with a particular solvent.

This organotin fluoride may be of any type. Typically, it is an alkyltin fluoride, more particularly a dialkyltin fluoride. Generally, organotin difluorides are used.

Particularly preferred starting materials include methyltin or dimethyltin fluorides, butyltin fluorides, and the octyltin and dioctyltin fluorides, more preferably dibutyltin difluoride.

It is important to appreciate that the particular technique for the preparation of the organotin fluoride may be of any type. Indeed, this is intended to represent that any suitable stannic compound and fluorinating agent may be used as starting materials, and specifically those indicated above.

However, the process of the invention is applied particularly well in the event that the fluorinating agent is hydrofluoric acid or ammonium fluoride. This is specifically the case in which the organotin fluoride is prepared by reacting a substrate of the organotin chloride type, for example with HF in water and in the presence of an alcohol, such as methanol.

Likewise in the event that a substrate of the same type is reacted with anhydrous HF.

The subject process is also suitable in the case that ammonium fluoride is used a the fluorinating agent and in particular ammonium difluoride, NH4P, with HP in an aqueous or alcohol solution.

The above three embodiments are especially well suited where the substrate is an alkyltin chloride.

The principal characteristic of the present invention is the treatment of an organotin fluoride thus prepared with a solvent which must have the following properties.

First, such solvent must be immiscible with the fluorinating agent used in the reaction with the substrate. Furthermore, as above indicated, the process according to the invention comprises a heating stage in which the medium containing the organotin fluoride, solvent and the fluorinating agent, is heated to a temperature at which the fluorinating agent is released or evolved therefrom.

This of course connotes that the solvent has a boiling point temperature higher than the heating temperature indicated above.

In the event that hydrofluoric acid or ammonium fluoride is used as the fluorinating agent, the boiling temperature of the solvent must be higher than that of such agent. In principle, the ease of application of the process of the invention will be greater with larger differences between the respective boiling points.

For example, in the specific case in which HF is the fluorinating agent, the boiling temperature of the solvent should be at least 110°C., and preferably at least 120° C.

In addition, the solvent must satisfy two conditions relative to the organotin fluoride. First, the solvent must be able to solubilize the organotin fluoride that is to be prepared. Secondly, it must permit the crystallization of the organotin fluoride. Finally, the solvent preferably should be inert with respect to the fluorinating agent.

Generally, aprotic solvents with low or no polarity are suitable.

One class of solvents suitable for use according to the invention comprises the aromatic hydrocarbons, and more particularly the chlorinated aromatic hydrocarbons.

Exemplary thereof are chlorobenzene, dichlorobenzene, in particular orthodichlorobenzene, xylene and toluene.

The different stages of the process of the invention will now be more fully described.

In the first embodiment of the invention, the organotin fluoride is admixed with the solvent. This mixing operation may be carried out by introducing a previously prepared organotin fluoride, i.e., one separated from its reaction medium and optionally dried, into the necessary amount of the solvent. More generally, the treatment is carried out immediately following the reaction for the preparation of the organotin fluoride.

In this case, the solvent is introduced into the reaction medium containing the organotin fluoride formed, the unreacted fluorinating agent and optionally an aqueous or alcohol phase, depending on the particular technique employed.

Once the organotin fluoride is mixed or placed into contact with the solvent, the resulting mixture is heated to a temperature at which the release of the fluorinating agent from the mixture is observed.

It will be appreciated that it is possible to simultaneously carry out admixing the solvent with the organotin fluoride and the heating operation.

At this stage in the process, the fluorinating agent still present and to be released, may be that remaining in the reaction medium of the preparation of the organotin fluoride, and/or that remaining, in particular, as an impurity with the organotin fluoride, especially if the latter had been prepared previously.

The temperature attained during the heat treatment depends on the fluorinating agent and the solvent. It typically ranges from 110. to 150.C, in particular if the fluorinating agent is HF.

The heating is continued until no further release of the fluorinating agent is observed.

At this stage in the process, a solution of the organotin fluoride in the solvent is typically obtained. The solution is then cooled to induce the crystallization of the organotin fluoride.

Once crystallization is completed, the product may be separated from the solvent by any suitable means. The solvent may then be recycled.

It is then preferable to wash the product obtained to eliminate, in particular, trace amounts of the solvent. A second solvent is generally used for this purpose.

This second solvent should be miscible with the first, and preferably have a low boiling point.

It thus may be selected from among the aliphatic or alicyclic halogenated hydrocarbons and ketones.

Particularly exemplary thereof are halogenated aliphatic or alicyclic hydrocarbons having a short chain $C_1$—$C_{14}$ moiety, especially those marketed under the trademark FLUGENE.

After washing, the product is dried by any known means, for example by a flowstream of dry air, at a temperature of about 70.C in the case of DBTF.

The grain size distribution of the product obtained in this manner may be adjusted by grinding, with such grain size distribution being a function of the intended application of the final product.

The second embodiment of the invention differs from the first embodiment described above essentially relative to the first stage thereof.

Indeed, a mixture containing the stannic substrate, the fluorinating agent and the solvent is initially formed. Once the mixture is formed, the conditions are adjusted such that the substrate will be reacted with the fluorinating agent to prepare the organotin fluoride. To facilitate the reaction, the mixture is preferably agitated.

The progress and the completion of the fluorination reaction may be monitored by observing the formation and release of the byproducts of the reaction, for example of HCl, if the fluorination is carried out using HF and a chloride substrate.

When the reaction is complete, the mixture is heated to induce the release of the residual fluorinating agent.

From this point, the process is continued as in the first embodiment. It should be appreciated that the above description relative to the first embodiment also applies to the second embodiment.

As above indicated, the present invention enables preparation of organotin compounds having a particular morphology.

Thus, in the case of the dialkyltin difluorides, these are produced in the form of platelets. With respect to uniform morphology, the platelets are essentially rectangular. Their length generally ranges from 25 to $\mu m 100$ $\mu m$. Their width ranges from 5 to 20 $\mu m$ and their thickness from 0.02 to 1 $\mu m$.

The final products are further characterized in that they have a DTA (differential thermal analysis) spectrum exhibiting an exothermic peak corresponding to the completion of decomposition of the alkyltin fluoride, situated at about 350° C, generally at 350°[9 ]% 20.C.

The characteristic spectrum is obtained under the following analytical conditions:

(i) Nitrogen flushing;

(ii) Increasing the temperature by 5° per minute to 600° C.;

(iii) DTA sensitivity of 0.2 mV.

As indicated above, the process of the invention provides a dibutyltin difluoride having the aforesaid morphological and DTA characteristics.

It was determined that such DBTF is especially well suited for hardcoating applications.

The DBTF according to the invention has a melting point of 158° C.

In order to further illustrate the present invention and the advantages thereof, the following specific examples are given, it being understood that same are intended only as illustrative and in nowise limitative.

EXAMPLE 1

500 g of dibutyltin chloride (DBTC) were contacted with 500 g anhydrous HF in an agitated reactor. Observation of the release of HCl made it possible to determine the completion of the fluorination which produced a solution of dibutyltin difluoride in anhydrous HF.

Orthodichlorobenzene was introduced into the reactor and distillation of anhydrous HF was commenced. A constant volume was thereby maintained in the reactor. Following the introduction of all of the solvent, the temperature was raised to 120° C. The dibutyltin difluoride was then in solution and the residual anhydrous HF was vaporized therefrom. After the absence of any further HF discharge had been ascertained, the solution of the dibutyltin difluoride in orthodichlorobenzene was transferred into a crystallizer. The cooling of the solution from 110° C. initiated the crystallization of the dibutyltin difluoride. Washing was carried out using FLUGENE 113 or methylene chloride and was followed by drying with dry air at 70° C. 420 g dibutyltin difluoride were obtained in this manner.

The final product was in the form of 50 $\mu$m by 15 $\mu$m platelets having a thickness of 0.5 $\mu$m. The Figure of Drawing shows the DTA spectrum of this final product, said spectrum having been obtained under the above conditions. The scale given on the abscissa is that of temperature in ° C. An exothermic peak at about 350° C. is clearly shown.

EXAMPLE 2

The procedure of Example 1 was repeated, but using orthoxylene as the solvent. The same amount of final product was obtained, having the same morphology m, as in Example 1.

EXAMPLE 3

In an agitated reactor, a solution of 500 g DBTC in one liter of orthoxylene was contacted with 500 g anhydrous HF at $-10°$ C. The reactor was heated to 25.C under agitation and under HF reflux. The release of HCl was observed to monitor the progress of the reaction. At the end of the HCl release, the temperature was increased to 120° C. by terminating the reflux and the fluorinating agent was thereby released.

A solution of DBTF in orthoxylene was obtained, which was cooled to crystallization at ambient temperature.

After filtration and washing with methylene chloride and drying in an oven at 70° C., 400 g of dibutyltin difluoride were recovered, having the same morphology as the product of Example $\mu$1.

While the invention has been described in terms of various preferred embodiments, the skilled artisan will appreciate the various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an organotin 2 fluoride having a controlled morphology, comprising reacting a stannic compound with a fluorinating agent, admixing the organotin fluoride thus produced in a solvent that is immiscible with said fluorinating agent but which solubilizes the organotin fluoride therein, subsequently or simultaneously heating the solvent medium to a temperature sufficient to release unreacted fluorinating agent therefrom, and cooling such solvent medium and thereby crystallizing therefrom said organotin fluoride having a controlled morphology.

2. A process for the preparation of an organotin fluoride having a controlled morphology, comprising intimately admixing a stannic compound, a fluorinating agent and a solvent that is immiscible with said fluorinating agent but which solubilizes desired organotin fluoride therein, whereby reacting said stannic compound with said fluorinating agent and, upon completion of such reaction, heating the reaction medium to a temperature sufficient to release unreacted fluorinating agent therefrom, and thence cooling such reaction medium and thereby crystallizing therefrom said organotin fluoride having a controlled morphology.

3. The process as defined by claims 1 or 2, said fluorinating agent comprising hydrofluoric acid or an ammonium fluoride.

4. The process as defined by claim 3, said fluorinating agent comprising anhydrous hydrofluoric acid.

5. The process as defined by claim 3, said fluorinating agent comprising ammonium difluoride.

6. The process as defined by claim 3, said solvent comprising an aprotic solvent having little or no polarity.

7. The process as defined by claim 6, said solvent comprising an aromatic hydrocarbon.

8. The process as defined by claim 7, said solvent comprising a chlorinated aromatic hydrocarbon.

9. The process as defined by claim 7, said aromatic hydrocarbon comprising chlorobenzene, dichlorobenzene, xylene o toluene.

10. The process as defined by claim 3, said final product organotin fluoride comprising an alkyltin fluoride.

11. The process as defined by claim 10, said alkyltin fluoride comprising a difluoride.

12. The process as defined by claim 11, said alkyltin difluoride comprising dibutyltin difluoride.

13. The process as defined by claim 4, said stannic compound comprising an organotin chloride.

14. The process as defined by claim 3, comprising separating said organotin fluoride crystals and washing same with a second solvent 15. The process as defined by claim 14, said second solvent being miscible with the first solvent 16. The process as defined by claim 15, said second solvent having a low boiling point.

17. The process as defined by claim 15, said second solvent comprising a halogenated aliphatic or alicyclic hydrocarbon or ketone.

18. An alkyltin difluoride comprising platelets having a length of 25 to 100 $\mu$m, a width of 5 to 20 $\mu$m, a thickness of 0.02 to 1 $\mu$m, and exhibiting a DTA spectrum having an exothermic peak at about 350° C.

19. The alkyltin difluoride as defined by claim 18, comprising dibutyltin difluoride.

20. The dibutyltin difluoride as defined by claim 19, having a melting point of about 158° C..

21. The product of the process as defined by claim 1

22. The product of the process as defined by claim 2.

* * * * *